(12) United States Patent
Ghanam et al.

(10) Patent No.: US 12,279,919 B2
(45) Date of Patent: Apr. 22, 2025

(54) TRACKER FOR A SURGICAL NAVIGATION SYSTEM

(71) Applicants: Stryker European Holdings I, LLC, Kalamazoo, MI (US); Scopis GmbH, Berlin (DE)

(72) Inventors: Fadi Ghanam, Schallstadt (DE); Christopher Özbek, Berlin (DE)

(73) Assignee: Stryker European Operations Limited, Carrigtwohill (IE)

( * ) Notice: Subject to any disclaimer, the term of this patent is extended or adjusted under 35 U.S.C. 154(b) by 648 days.

(21) Appl. No.: 15/930,508

(22) Filed: May 13, 2020

(65) Prior Publication Data

US 2020/0360106 A1 Nov. 19, 2020

(30) Foreign Application Priority Data

May 15, 2019 (EP) .................................... 19174704

(51) Int. Cl.
*A61B 90/00* (2016.01)
*A61B 10/02* (2006.01)
*A61B 34/20* (2016.01)

(52) U.S. Cl.
CPC .......... *A61B 90/39* (2016.02); *A61B 10/0233* (2013.01); *A61B 34/20* (2016.02); *A61B 2034/2055* (2016.02); *A61B 2034/2072* (2016.02); *A61B 2090/3937* (2016.02); *A61B 2090/3945* (2016.02); *A61B 2090/3983* (2016.02)

(58) Field of Classification Search
CPC .................... A61B 34/20; A61B 90/39; A61B 2090/3904–3995; A61B 17/00234; A61B 17/3403
See application file for complete search history.

(56) References Cited

U.S. PATENT DOCUMENTS

| | | | |
|---|---|---|---|
| 7,840,256 | B2 | 11/2010 | Lakin et al. |
| 8,663,204 | B2 | 3/2014 | Lechner et al. |
| 9,179,984 | B2 | 11/2015 | Teichman et al. |

(Continued)

FOREIGN PATENT DOCUMENTS

| | | | |
|---|---|---|---|
| CN | 104887327 A | | 9/2015 |
| CN | 107693131 A | | 2/2018 |

(Continued)

OTHER PUBLICATIONS

English language abstract for EP 2 246 005 extracted from espacenet.com database on Jun. 8, 2020, 2 pages.

(Continued)

*Primary Examiner* — Angela M Hoffa
*Assistant Examiner* — Younhee Choi
(74) *Attorney, Agent, or Firm* — Howard & Howard Attorneys PLLC

(57) ABSTRACT

A tracker for a surgical navigation system is provided. The tracker includes one or more markers for determining a position of the tracker and an attachment element configured to releasably attach the tracker to a surgical tool. The attachment element includes an opening for receiving the surgical tool, wherein the opening defines a longitudinal axis. The one or more markers are coupled to the attachment element so as to be symmetrically arranged with respect to the longitudinal axis.

14 Claims, 5 Drawing Sheets

(56) References Cited

U.S. PATENT DOCUMENTS

| | | |
|---|---|---|
| 9,393,039 B2 | 7/2016 | Lechner et al. |
| 10,034,713 B2 | 7/2018 | Yang et al. |
| 10,108,833 B2 | 10/2018 | Hong et al. |
| 10,350,013 B2* | 7/2019 | Crawford ............... A61B 34/20 |
| 2004/0054489 A1* | 3/2004 | Moctezuma De La Barrera ........ G16Z 99/00 702/105 |
| 2005/0131426 A1* | 6/2005 | Moctezuma de la Barrera .......... A61B 34/20 606/130 |
| 2005/0203536 A1 | 9/2005 | Laffargue et al. |
| 2006/0072124 A1 | 4/2006 | Smetak et al. |
| 2007/0016009 A1* | 1/2007 | Lakin ..................... A61B 90/39 600/424 |
| 2011/0263971 A1 | 10/2011 | Nikou et al. |
| 2014/0214086 A1* | 7/2014 | Benson ................. A61B 17/885 606/86 R |
| 2014/0275955 A1* | 9/2014 | Crawford ............... A61B 5/066 600/409 |
| 2016/0270863 A1 | 9/2016 | Makower |
| 2017/0007349 A1* | 1/2017 | Solar ..................... A61B 34/20 |
| 2018/0014888 A1* | 1/2018 | Bonny ................... A61B 34/20 |
| 2018/0014890 A1* | 1/2018 | Stanton ................. A61B 90/39 |
| 2018/0221098 A1 | 8/2018 | Forsyth et al. |
| 2018/0221108 A1 | 8/2018 | Broers et al. |
| 2019/0209080 A1* | 7/2019 | Gullotti ............... A61B 17/7035 |
| 2019/0380811 A1* | 12/2019 | Kim ........................ A61C 1/084 |
| 2020/0129049 A1* | 4/2020 | Panitz ................ A61B 1/00142 |
| 2020/0289224 A1* | 9/2020 | Johnson ................. A61B 90/11 |

FOREIGN PATENT DOCUMENTS

| | | |
|---|---|---|
| CN | 108348302 A | 7/2018 |
| EP | 2246005 A1 | 11/2010 |
| WO | 2012152879 A1 | 11/2012 |
| WO | 2016139638 A1 | 9/2016 |

OTHER PUBLICATIONS

English language abstract and machine-assisted English translation for CN 104887327 A extracted from espacenet.com database on Mar. 21, 2024, 10 pages.

English language abstract for CN 107693131 A extracted from espacenet.com database on Mar. 21, 2024, 2 pages.

English language abstract for CN 108348302 A extracted from espacenet.com database on Mar. 21, 2024, 1 page.

English language abstract and machine-assisted English translation for WO 2012/152879 A1 extracted from espacenet.com database on Mar. 21, 2024, 15 pages.

* cited by examiner

TRACKER FOR A SURGICAL NAVIGATION SYSTEM

PRIORITY CLAIM

This application claims priority under 35 U.S.C. § 119 to European Patent Application No. 19174704.7, filed May 15, 2019, the entire contents of which are hereby incorporated by reference.

TECHNICAL FIELD

The present disclosure generally relates to a tracker for use in a surgical navigation system. In particular, a tracker which is configured to be releasably attachable to a surgical tool is presented.

BACKGROUND

During surgery, a surgeon often uses surgical tools that have to be inserted into the body of a patient. Once inside the patient's body, the surgeon loses vision of the tip of the tool. In order to help the surgeon navigate the tool in such a case, a surgical navigation system can be used that tracks the tool and provides visual or acoustic guidance to the surgeon.

One way to track the tool is to attach a tracker onto the tool. A camera in the operating room detects the tracker and generates data that is used to calculate the position of the tracker and, therefore, of the tool. Commonly, the patient is tracked also, which enables calculating the position of the tool relative to the patient.

Surgical navigation can be carried out using passive or active trackers. A passive tracker comprises markers that reflect light. The reflected light can be detected by the camera. An active tracker generates light (e.g., via a light-emitting diode) that can be detected by the camera.

Furthermore, known navigated tools can be tracked by either using integrated markers or by attaching an external tracking device.

Integrated markers have the advantages of being light-weighted, well-balanced and having a small footprint. However, since the surgical tool with the tracker is offered as an integrated tracking system, when the tracking technology is changed the surgeon has to get used to the new system as a whole and can typically not continue to use the surgical tool he is used to.

In comparison, on the one hand, external tracking devices provide the advantage that they can flexibly be used in combination with different types of surgical tools so that the surgeon does not have to switch to a new surgical tool he is not familiar with when changing the tracking technology. On the other hand, handling of the else familiar surgical tool is affected adversely for the surgeon with the external tracking device attached thereto, since the surgical tool with the attached external tracking device is much heavier than without the external tracking device being attached and is off balance.

SUMMARY

There is a need for a tracker that solves one or more of the aforementioned problems.

According to one aspect, a tracker for a surgical navigation system is provided. The tracker comprises one or more markers for determining a position of the tracker and an attachment element configured to releasably attach the tracker to a surgical tool. The attachment element comprises an opening configured for receiving the surgical tool, wherein the opening defines a longitudinal axis. The one or more markers are coupled to the attachment element so as to be symmetrically arranged with respect to the longitudinal axis.

The one or more markers may be or may include one more passive markers. Thus, they may be reflective to light of a predetermined light spectrum, such as infrared light, for example. Based on the reflected light, a position of the tracker can be determined by the navigation system.

The one or more markers may be or may include one or more active markers. Thus, the active markers are configured to emit light of a predetermined light spectrum, such as infrared light, for example. For example, the active trackers may include light emitting diodes. Based on the emitted light, a position of the tracker can be determined. Active and passive markers may be combined in the one or more markers.

By provision of the attachment element, the tracker can be releasably attached to a surgical tool. Thus, the tracker presented herein is an external tracker that can be associated with any surgical tool that is intended to be tracked. The shape and the dimensions of the opening of the attachment element may be adapted to the shape and dimensions of the surgical tool intended to be used with the tracker. Therefore, the opening is dimensioned to receive the surgical tool. The opening of the attachment element defines a longitudinal axis, which may extend in a longitudinal direction of the attachment element. The opening may extend through the whole attachment element so as to be a through-hole.

In some variants, the longitudinal axis may also define the direction along which the surgical tool can be slid in the opening of the attachment element for being attached to the tracker. In other variants, the tracker may be attached to the surgical tool by moving the tracker in a direction different from the direction defined by the longitudinal axis.

The one or more markers may be directly coupled to the attachment element. Alternatively, they may be coupled to the attachment element via other coupling elements.

The one or more markers are arranged symmetrically with respect to the longitudinal axis of the attachment element, thus providing a well-balanced arrangement. The one or more markers may thus be arranged axisymmetric with respect to the longitudinal axis.

The tracker disclosed herein may be used in connection with a biopsy needle. The tracker disclosed herein may be also used in connection with other surgical tools, for example for tracking an insertion depth of semi-rigid straight objects like shunts into a bodily cavity. The tracker may be also used in connection with a surgical drill for tracking an insertion depth of the drill. In general, an insertion depth and trajectory of any rigid straight instrument can be tracked by the tracker.

The attachment element may comprise a sleeve defining the opening for receiving the surgical tool. Thus, the attachment element may comprise a hollow elongated body which is at least partly surrounded by a wall.

In one variant, the one or more markers may be arranged on the attachment element on or along the longitudinal axis defined by the opening. In this variant, each of the one or more markers is directly arranged on the attachment element. The one or more markers are arranged so as to extend along the longitudinal axis. Two or more markers may be arranged with a distance between the individual markers. At least one of the one or more markers may be arranged at a longitudinal end of the attachment element.

In this variant, the one or more markers may be configured and arranged so as to be rotationally symmetrical to the longitudinal axis. For example, the markers may each form a sphere or disk, and they may be arranged on the attachment element so that the attachment element goes through the center of each of the spheres or disks.

In another variant, the one or more markers comprise two or more markers, which may be arranged at a distance from the attachment element. In this variant, the markers may be coupled to the attachment element via coupling elements such as mounting posts or wings. The two or more markers may be arranged so as to be symmetrically arranged with respect to the longitudinal axis, for example so as to be axisymmetric to the longitudinal axis.

In an aspect of the other variant, the two or more markers may be arranged on mounting posts. The mounting posts may be coupled to the attachment element so as to be oriented substantially perpendicular to the longitudinal axis of the attachment element. In this aspect, the markers are coupled via the mounting posts with the attachment element. The markers may be releasably mounted to the mounting posts, so as to be separately sterilizable or disposable. The markers may be also fixedly connected to the mounting posts.

The mounting posts and the attachment element may be configured as a one-piece part (e.g., using injection molding). The mounting posts and the attachment element may be further made of the same material or materials. For example, the mounting posts and the attachment element may be made of metal or metal materials, for example of steel or stainless steel. The mounting posts and the attachment element may be also made from a plastics material (e.g., as an injection-molded part). The configuration as a one-piece part enables a comfortable handling of the tracker and results in a cost-efficient production.

The attachment element may be configured to be attachable to the surgical tool by a clip mechanism. The attachment element may have an open lateral side, via which the surgical tool can be inserted, by moving it in a direction perpendicular to the longitudinal axis, into the opening of the attachment element. If the attachment element is configured as a sleeve, the sleeve may be formed with an open lateral side via which the surgical tool may be received. The material of the attachment element may be flexible enough for the attachment element being clippable on the surgical tool. For example, the attachment element may be made from a plastics material, such as polyether ether ketone (PEEK). Due to the clip mechanism, no additional fixation member may be required for fixing the tracker to the surgical tool.

The tracker may further comprise a fixation member for positionally fixing the tracker with respect to the surgical tool. For example, after the tracker with the attachment element is slid on the surgical tool, the tracker may be secured in place by the fixation member.

The fixation member may comprise a screw element. The screw element may act on the attachment mechanism so as to clamp the attachment mechanism to the surgical tool. The screw element may directly act on the surgical tool so as to fix the tracker with respect to the surgical tool. The fixation member may comprise a plastics material, such as PEEK, for example. The fixation member may be an element separate from the attachment mechanism or be comprised by the attachment mechanism. For example, the fixation member may be mounted on the attachment element, thereby forming a separate element.

The tracker may comprise a stopper element configured to cooperate with a guidance (e.g., a guiding tube) so as to limit an insertion depth of the surgical tool. In particular, during surgery, a guidance is often used to guide the movement of the surgical tool within the patient, i.e., the surgical tool with the tracker is inserted into the guiding member. The stopper element is configured to cooperate with the guidance so as to stop the movement of the surgical tool within the guidance when having reached a predetermined position. The predetermined position is defined by a target value for at least one of the relative position and orientation between the stopper element/tracker and the target surgery area in a patient's body. The target value for the at least one of the relative position and orientation is, for example, given when a tip of the surgical tool has reached the target surgery area.

The stopper element may be mounted to the attachment element at a longitudinal end of the attachment element. Thus, the stopper element of the surgical tool may be integrated into the tracker. The stopper element may be mounted releasably or fixedly to the attachment element. The stopper element may also comprise a screw element or any other fixation means for releasably fixing the stopper element to the attachment element.

Alternatively, the attachment element may form a stopper element configured to cooperate with a guiding tube so as to limit an insertion depth of the surgical tool. Thus, the attachment element does not only have the function to attach the tracker to the surgical tool, but also to limit the insertion depth of the surgical tool.

In both alternatives, i.e., when the attachment element forms the stopper element or when the stopper element is configured as a separate element, the stopper element may also form the fixation member. Thus, no separate fixation member is needed, but the stopper element comprises a fixation means for positionally fixing the attachment element to the surgical tool. This fixation means may be the same fixation means by which the stopper element is secured to the attachment element, or it may be a separate fixation means.

Further, in both alternatives, i.e., when the attachment element forms the stopper element or when the stopper element is configured as a separate element, the stopper element is combined with the tracker thereby enabling double checking a position of the stopper element. Specifically, before using a surgical tool comprising the tracker, the position of the stopper element may be determined or validated. For example, the stopper element may be positioned on the surgical tool so that a distance between a tip of the surgical tool and a proximal stop surface of the stopper element substantially corresponds to a target insertion depth of the surgical tool, in particular to an insertion depth of the surgical tool within a guidance, at which the insertion is intended to be stopped for performing the surgery. The positioning of the stopper element, i.e., of the proximal stop surface of the stopper element, with respect to the tip of the surgical tool may be determined by means of a ruler. During surgery, the position and/or orientation of the tracker can be determined by means of the one or more markers, both with respect to a camera and a patient's body.

Since the stopper element of the present disclosure is integrated into the tracker, the relative position between the proximal stop surface of the stopper element and the one or more markers can be calibrated or determined prior to surgery. Therefore, based on the position and/or orientation of the tracker, also the position and/or orientation of the stopper element (i.e., its stop surface) can be determined, also both with respect to the camera and the patient's body.

Hence, it may be checked, for example, based on these data, whether the stopper element has a relative position and/or orientation to the target surgery area within the patient's body which corresponds to a target value for the relative position and/or orientation between the stopper element/ tracker and the target surgery area in a patient's body. The target value for the relative position and/or orientation is given when the tip of the surgical tool has reached the target surgery area. The target valve may be planned pre-operatively.

In case a surgical tool such as a biopsy needle is accidentally bent, the proximal stop surface of the stopper element may abut against the guiding tube before the intended insertion depth is reached. That the intended insertion depth is not reached may be verified by means of the calculated position and orientation data based on the light received from the tracker. Based on these data, the surgeon may then decide whether he or she wants to stop an insertion of the surgical tool, corresponding to the "warning" of the stopper element, or whether he or she wants to continue inserting. Thus, since the stopper element is integrated into the tracker and the distance between the stopper element and the one or more markers is known, the position of the stopper element may be checked or tracked during the surgery, in addition to the pre-surgery process where the position of the stopper element is validated.

The markers may include one or more passive markers. One or more of the one or more markers may have a generally spherical shape. One or more of the plurality of markers may generally have a disk-shape. One or more active markers may also be used.

The one or more markers may be exactly two markers, but the one or more markers may be also more than two markers, for example three markers, four markers or five markers.

One or more, or all, of the one or more markers may be detachable from the attachment element. To this end, complementary interfaces may be provided at each detachable marker and the attachment element.

According to a second aspect, a surgical system is provided. The surgical system comprises a tracker as described herein and the surgical tool releasably coupled to the tracker so that the plurality of markers are symmetrically arranged with respect to the longitudinal axis of the attachment element.

The surgical system may have a longitudinal axis which coincides with the longitudinal axis of the attachment element. The longitudinal axis may be the longitudinal axis of a surgical rod, of a needle or of any other longitudinally extended member of a surgical tool. Thus, the plurality of markers may be symmetrically arranged with respect to the longitudinal axis of the surgical tool, providing a well-balanced surgical tool.

The surgical tool may have a longitudinal member for receiving the tracker. For example, the surgical tool may be a biopsy needle. Biopsy needles are known surgical tools and are used for taking tissue samples via a biopsy window at the tip of the biopsy needle.

According to a third aspect, a surgical system is provided in which the tracker comprises a stopper element, and which comprises a precision arm which has a guidance for receiving the surgical tool so as to be linearly movable in one direction and in a direction opposite to the one direction. The precision arm is configured to be moved three-dimensionally, in particular to move the guidance three-dimensionally. The guidance comprises an abutment surface which cooperates with a proximal stop surface of the stopper element so as to limit the linear movement of the surgical tool within the guidance in one direction. The guidance may comprise a guiding tube or a plurality of co-axial bores into which the surgical tool can slidably be inserted. The guidance may have a surface for cooperating with the stopper element so as to limit an insertion depth within the guiding tube.

According to a fourth aspect, a surgical navigation system is provided which comprises a tracker or a surgical tool system as described herein, and an optical sensor capable of detecting light reflected or emitted by the plurality of markers and of generating a sensor signal indicative of the detected light.

The optical sensor may comprise at least one camera. The optical sensor may comprise a mono camera and/or a stereo camera. The optical sensor may be configured to have an increased sensitivity for an optical spectrum reflected or emitted by the plurality of markers. The optical spectrum many be the Infrared (IR) spectrum or the visible spectrum, or another spectrum. The higher sensitivity may be realized by an optical filter or circuitry that filters sensor signal data dependent on its associated wavelength.

The surgical navigation system may further comprise a navigation controller capable of receiving the sensor signal and at least one of registering and tracking the tracker based on the received sensor signal.

According to a fifth aspect, a method of operating a surgical navigation system is provided. The surgical navigation system comprises an optical sensor and a tracker with one or more markers for determining a position of the tracker, an attachment element configured to releasably attach the tracker to a surgical tool, and a stopper element configured for cooperating with a guidance so as to limit an insertion depth of the surgical tool. The attachment element comprises an opening for receiving the surgical tool, wherein the opening defines a longitudinal axis. The one or more markers are coupled to the attachment element so as to be symmetrically arranged with respect to the longitudinal axis. The method comprises the steps of determining a relative position between a proximal stop surface of the stopper element and at least one of the one or more markers; detecting, by the optical sensor, light reflected or emitted by the one or more markers; calculating at least one of a position and an orientation of the tracker in a coordinate system of the surgical navigation system based on the detected light; and calculating at least one of a position and an orientation of the proximal stop surface of the stopper element in the coordinate system of the surgical navigation system based on the determined relative position and the at least one of the calculated position and orientation of the tracker.

The relative position between the proximal stop surface of the stopper element and at least one of the one or more markers may be defined by a distance between the proximal stop surface and the at least one marker, and how the proximal stop surface is oriented with respect to the at least one marker.

Calculating the position and/or orientation of the tracker in a coordinate system of the surgical navigation system may include calculating the position and/or orientation of the tracker relative to the optical sensor. The subsequent step regarding the proximal stop surface may then include calculating the position and/or orientation of the proximal stop surface of the stopper element relative to the optical sensor.

Usually, also the patient's body is tracked by means of the optical sensor, so that the position and/or orientation of the patient's body relative to the optical sensor may be calculated. Consequently, the position and/or orientation of the proximal stop surface of the stopper element relative to the patient's body may be determined based on the calculated position and/or orientation of the proximal stop surface relative to the optical sensor and the position and/or orientation of the patient's body relative to the optical sensor.

Determining the position and/or orientation of the proximal stop surface relative to the patient's body may include determining the position and/or orientation of the proximal stop surface of the stopper element relative to a target surgery area within the patient's body. Then, it may checked whether the position and/or orientation of the proximal stop surface of the stopper element relative to a target surgery area within the patient's body corresponds to a target relative position and/or target relative orientation of the proximal stop surface of the stopper element relative to the target surgery area. In particular, the target relative position and/or target relative orientation of the proximal stop surface relative to the target surgery area is the position and/or orientation of the proximal stop surface with respect to the target surgery area when the tip of the surgical tool has reached the target surgery area when inserting the surgical tool into the patient's body.

In a variant of the fifth aspect, the tracker may be part of a surgical tool system comprising the tracker and a surgical tool configured to be releasably coupled to the tracker so that the one or more markers are symmetrically arranged with respect to the longitudinal axis of the attachment element. The method may comprise the steps of coupling the tracker with the surgical tool, and fixing the tracker to the surgical tool so that a position and/or orientation of the proximal stop surface of the stopper element relative to a tip of the surgical tool corresponds to a target relative position and/or target relative orientation.

In one variant, the position of the stopper element may be double checked. For example, if it is decided that the position and/or orientation of the proximal stop surface of the stopper element relative to a target surgery area within the patient's body corresponds to the target relative position and/or target relative orientation of the proximal stop surface of the stopper element relative to the target surgery area, the stopper element should abut against the abutment surface of the guidance. Or, vice versa, if the stopper element abuts against the abutment surface of the guidance thereby limiting a further insertion of the surgical tool, the position and/or orientation of the proximal stop surface of the stopper element relative to a target surgery area within the patient's body determined should correspond to the target position and/or target orientation of the proximal stop surface of the stopper element relative to the target surgery area. If this is not the case, an error or defect might be present. For example, the surgical tool such as the biopsy needle might be accidentally bent, or the tracker might not be correctly positioned to the surgical tool. In such cases, the surgical navigation system may output a warning.

BRIEF DESCRIPTION OF THE DRAWINGS

Further details, advantages and aspects of the present disclosure will become apparent from the following embodiments taken in conjunction with the drawings, wherein.

DETAILED DESCRIPTION

Figure 1:
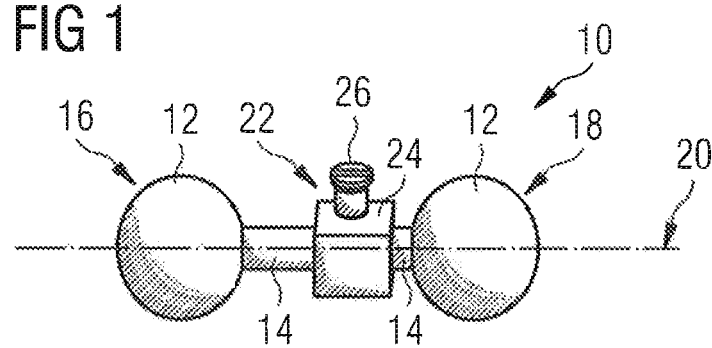
FIG. 1 shows a first embodiment of a tracker.

FIG. 1 shows a first embodiment of a tracker for a surgical navigation system. The tracker 10 comprises one or more markers 12 and an attachment element 14 on which the one or more markers 12 are mounted. In the embodiment of FIG. 1, two markers 12 are provided, and the markers 12 each have the shape of a sphere. In an alternative embodiment, one of the two markers 12 may be omitted.

The markers 12 are mounted on opposed longitudinal ends 16, 18 of the attachment element 14 to the attachment element 14. The attachment element 14 of FIG. 1 defines a longitudinal opening (not illustrated here) through the interior of the attachment element 14. The opening extends in a longitudinal direction along a longitudinal axis 20. The opening is configured for receiving a surgical tool such as a biopsy needle. In the example of FIG. 1, the attachment element 14 has a round outer cross-section. The attachment element 14 may also have a square or rectangular outer cross-section. The markers 12 have a longitudinal opening which extends therethrough for mounting the markers to the attachment element and which has a corresponding round or rectangular cross-section. In case of rectangular cross-sections, the markers 12 are mounted non-rotatably on the attachment element 14.

In the embodiment of FIG. 1, the markers 12 are shown to be passive markers which are configured to reflect light, in particular light of a predetermined spectrum such as IR light. However, the tracker 10 of FIG. 1, as well as all tracker embodiments disclosed herein, may be also equipped with active trackers which are configured to emit light, in particular light of a predetermined spectrum, such as IR light.

The opening extending through the attachment element 14 for receiving the surgical tool has a cross-section that is adapted to the outer shape of the surgical tool intended to be used in combination with the tracker 10. For example, in the case of a biopsy needle, the opening has a round cross-section. In each case, the cross-sectional dimensions of the opening are such that the surgical tool intended to be used in combination with the tracker can be inserted into the opening of the attachment element. The opening is configured as a through-opening, thus extending over the whole axial length of the attachment element 14. Consequently, the tracker 10 is formed as a sleeve which, when being received by the surgical tool, can be slidably moved along the surgical tool.

As can be further seen in FIG. 1, the tracker 10 also comprises a fixation member 22 for positionally fixing the tracker with respect to the surgical tool. In the present embodiment, the fixation member 22 is mounted on the attachment element 14. In particular, the fixation member 22 is also configured as a sleeve 24 that is, as an option, slidable along the longitudinal axis 20 of the attachment element 14.

The fixation member 22 comprises a screw 26 rotatably received by the sleeve 24 of the fixation member 22. By fastening of the screw 26, the attachment element 14 can be clamped to a surgical tool. In this case, the attachment element 14 should be made of a deformable material. The attachment element 14 may be also fixed to a surgical tool by the screw 26 of the fixation member 22 directly acting on the surgical tool. In that case, the attachment element 14 may have an aperture (not shown) for the screw and the attachment element 14 may be also formed of a rigid material. It will be appreciated that the fixation member 22 could be configured otherwise, for example so as to be activated and deactivated manually (without requiring a screw driver). To this end, the fixation member 22 may be provided with a lever.

As is further illustrated in FIG. 1, the markers 12 are arranged along the longitudinal axis 20 of the attachment element 14. In particular, each of the markers 12 of the one or more markers 12 is symmetrically arranged with respect to the longitudinal axis 20 of the attachment element 14. More particularly, each of the markers 12 is arranged so as to be rotationally symmetrical to the longitudinal axis 20.

Figure 2:
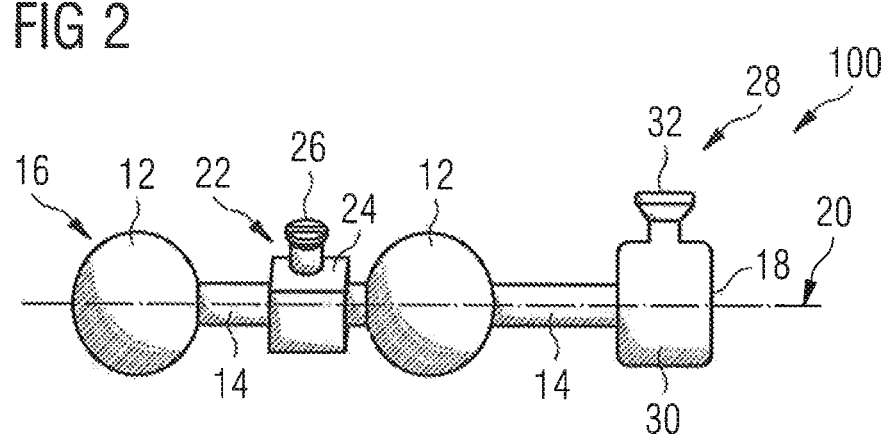
FIG. 2 shows a second embodiment of a tracker which comprises a stopper element.

FIG. 2 shows a second embodiment of the tracker 10 of FIG. 1. The tracker 100 of FIG. 2 corresponds to the tracker 10 of FIG. 1, with the exception that a stopper element 28 is additionally provided that is attached to the attachment element 14. The stopper element 28 is used for limiting an insertion depth of a surgical tool equipped with the tracker 100. Specifically, the stopper element 28 is configured to cooperate with a guidance of, for example, a precision arm, such as a guiding tube or guide bores for receiving a surgical tool to which the tracker 100 is attached. The stopper element 28 is configured to cooperate with the guidance so as to limit an insertion depth of the surgical tool. The stopper element 28 is attached to the longitudinal end 18 of the attachment element 14. Consequently, one of the markers 12 of the two markers 12 is no longer provided at the longitudinal end 18 of the attachment element 14, but is moved in a direction to the center of the attachment element 14 in a longitudinal direction of the attachment element 14. Similar to the fixation member 22, the stopper element 28 is configured as a sleeve 30 which can be received by the attachment element 14 and which comprises a screw 32 for fixing the stopper element 28 to the attachment element 14.

The stopper element 28 may be also fixed to the attachment element 14 by other means than the screw 32, for example by means of a Luer-Lock connection. The stopper element 28 may be also configured so as to be fixedly connected to the attachment element 14, for example by gluing. The stopper element 28 may be also integrally formed with the attachment element 14. In these cases, there is no need for a fixation element such as the screw 32.

The fixation member 22, or at least the sleeve 24 of the fixation member 22, and/or the stopper element 28 may be made from plastics material. For example, the plastics material may be PEEK, which is characterized by being resistive to many chemicals, being biocompatible and being repeatedly sterilizable. The plastics material may be also polyphenylene sulfone (PPSO2). Typical materials of the attachment element 14 are metal materials, such as steel or stainless steel.

Figure 3:
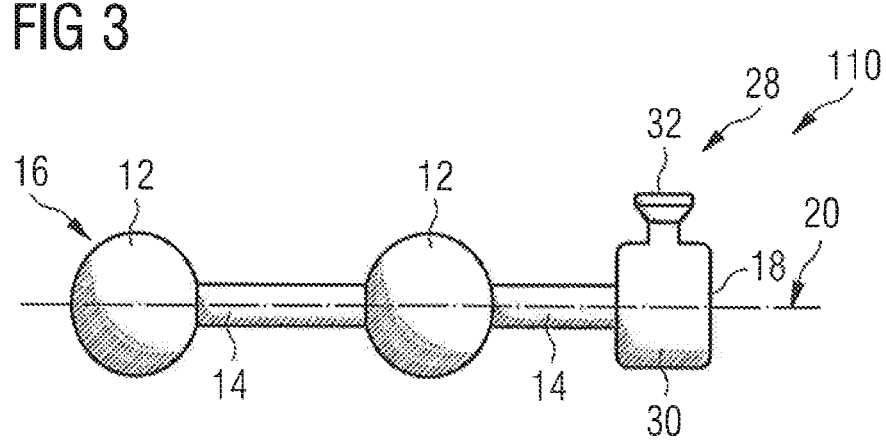
FIG. 3 shows a modified version of the second embodiment of FIG. 2, in which the stopper element also has the function of the fixation member.

FIG. 3 shows a modified version of the tracker 100 of FIG. 2. The tracker 110 corresponds to the tracker 100 of FIG. 2, with the exception that the fixation member 22 is no longer provided. Instead, the attachment element 14 can be fixed to a surgical tool such as a biopsy needle by means of the screw 32 of the stopper element 28, or by any other fixation means such as a Luer-Lock connection.

Figure 4:
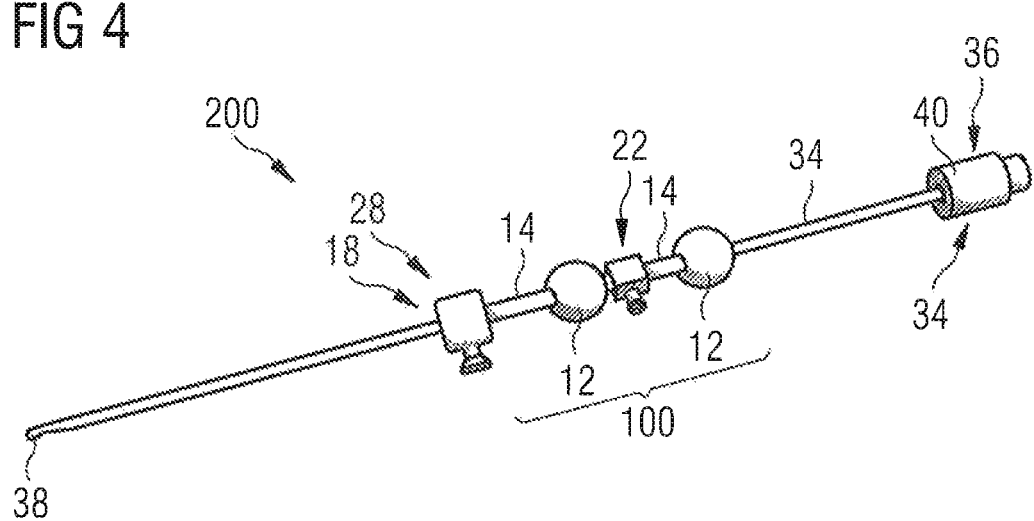
FIG. 4 shows an embodiment of a surgical tool system comprising the tracker of FIG. 2.

FIG. 4 shows a surgical tool system 200 with a surgical tool, here a biopsy needle 34, to which the tracker 100 as is shown in FIG. 2 has been attached. The biopsy needle 34 further comprises at its longitudinal end 36 opposite to a tip 38 of the needle 34 a grip 40 allowing the surgeon to handle the biopsy needle 34. As can be seen in FIG. 4, the tracker 100 is slid on the biopsy needle 34 and is positionally attached to the biopsy needle 34 by the screw 26 of the fixation member 22 clamping or fixing the tracker 100 to the biopsy needle 34. Furthermore, the stopper element 28 is provided at the longitudinal end 18 of the tracker 100 being proximal to the tip 38 of the biopsy needle 34. The outer cross-sectional dimensions of the stopper element 28 are large enough to limit an insertion depth of the biopsy needle 34 in a guiding tube or other guidance. The guiding tube may be attached to a precision arm having a fixed position relative to the patient to be treated. As such, the axial location of the stopper element 28 relative to the guidance together with the three-dimensional position and orientation of the guidance relative to a patient determine how deep the needle 34 is (allowed to be) inserted into the patient's body.

The tracker 100 of FIG. 4 can be also replaced with the tracker 10 of FIG. 1. In that case, a separate stopper element should be provided on the surgical tool.

The tracker 10 or 100 may be also mounted to the surgical tool at an opposed side of the grip 40. Thus, the tracker 10 or 100 100 may not be mounted on the left side of the grip 40 with respect to FIG. 4, but on the right side of the grip 40 with respect to FIG. 4, for example on an axial extension of the grip 40 (not illustrated here). In that case, there is no need for the stopper element 28 to be provided at the tracker 100, and a separate stopper element as known from the prior art could be attached at the surgical tool such as the biopsy needle.

Figure 5:
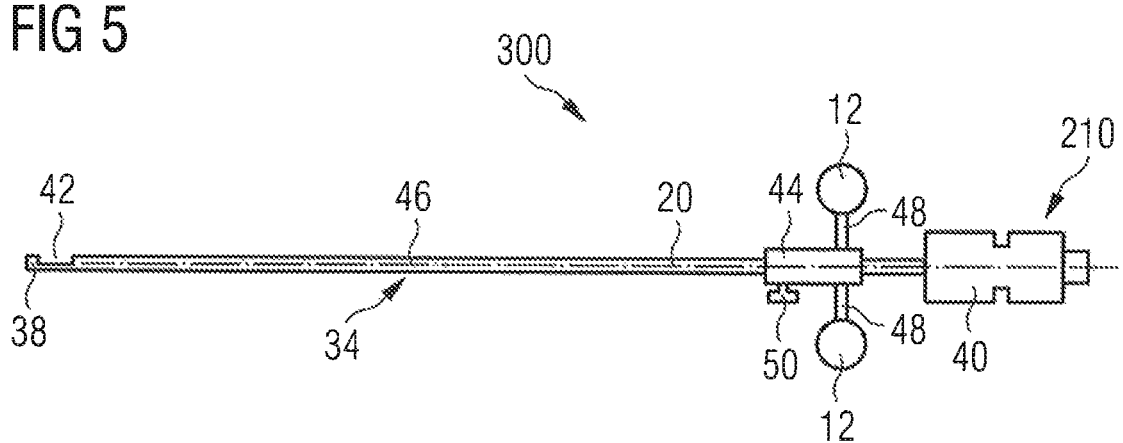
FIG. 5 shows another embodiment of a surgical tool system comprising a tracker with markers provided on mounting posts.

FIG. 5 shows a surgical tool system 210 with another embodiment of a tracker 300. The tracker 300 of FIG. 5 is again shown to be attached to a biopsy needle 34, but, according to the present disclosure, the tracker 300 can also be used in combination with other surgical tools having a generally longitudinal extension. Similar to the biopsy needle 34 of FIG. 4, the biopsy needle 34 of FIG. 5 comprises a tip 38 (with a biopsy window 42) at its one longitudinal end and an operational grip 40 at its other longitudinal end.

Similar to the tracker of FIGS. 1 to 4, the tracker 300 of FIG. 5 is slid on the biopsy needle 34. Specifically, the tracker 300 comprises an attachment element 44 with an opening for receiving the surgical tool, here the biopsy needle 34, wherein the opening defines a longitudinal axis 20. The longitudinal axis 20 of the attachment element 44, which is configured as a sleeve, coincides with the longitudinal axis 46 of the biopsy needle 34. Laterally to the attachment element 44 and the biopsy needle 34 and at a distance from the attachment element 44 and the biopsy needle 34 the plurality of markers 12 is arranged. In the embodiment of FIG. 5, at least two markers 12 are provided. Here, two markers 12 are provided. Furthermore, in the embodiment of FIG. 5, the markers 12 are configured as spheres. The markers 12 are attached to mounting posts 48, wherein the mounting posts 48 again are attached to the attachment element 44. In particular, the mounting posts 48 are arranged to be substantially perpendicular to the longitudinal axis 20 of the attachment element 44. The two markers 12 are equally designed and arranged with the same distance from the attachment element 44. Hence, the plurality of markers 12 is arranged symmetrical with respect to the longitudinal axis 20 of the attachment element and to the longitudinal axis 46 of the biopsy needle 34.

In the embodiment of FIG. 5, the attachment element 44 also has the function of the above-described stopper element to limit an insertion depth of the surgical tool. Thus, no separate stopper element as in FIGS. 2 and 3 is provided, but the attachment element 44 integrally forms the stopper element. In a similar manner as the stopper element of FIGS. 2 to 4, the stopper element of FIG. 5 (which is also the attachment element) comprises a screw 50 for fixing the tracker 300 to the surgical tool 34. Thus, no separate fixation member is needed.

Figure 6:
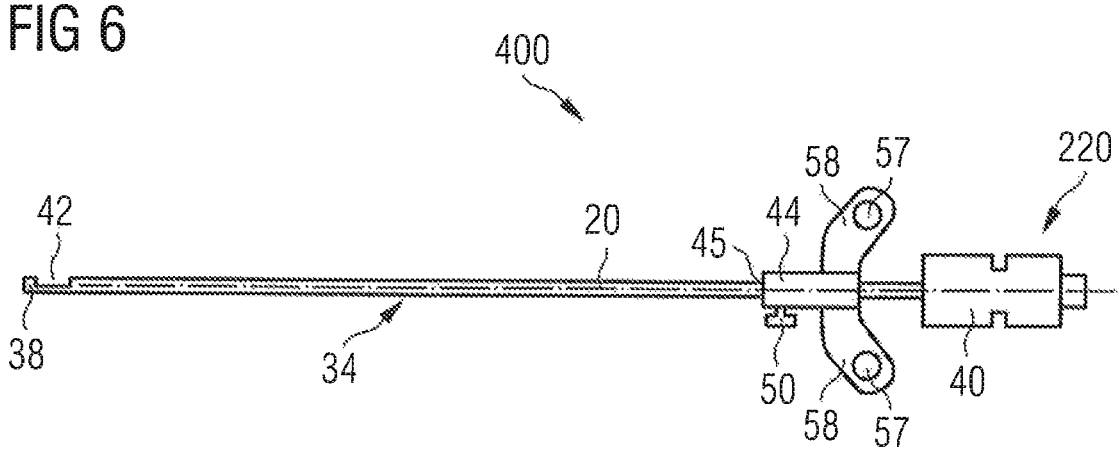
FIG. 6 shows a modified embodiment of the surgical tool system of FIG. 4.

FIG. 6 shows a surgical tool system 220 with a modified version of the tracker 300 shown in FIG. 5. Specifically, the tracker 400 of FIG. 6 differs from the tracker 300 of FIG. 5 in that the markers 57 are disk-shaped and are not coupled to the attachment element 44 by mounting posts, but via wings 58. In a similar manner as the spherical markers 12 of FIG. 5, the disk-shaped markers 57 of FIG. 6 are symmetrically arranged with respect to the longitudinal axis 20 of the attachment element 44 and located on the wings 58 that extend from the attachment element 44 in a direction away from the attachment element 44, i.e., in a direction substantially perpendicular to the direction of the longitudinal axis 20. Thus, also the disk-shaped markers 47 are laterally provided to the attachment element 44, and not axially as the markers of FIGS. 1 to 4.

The attachment element 44 and the mounting posts 48 or wings 58 may be made of metal, such as steel or stainless steel. Further, also in the embodiments of FIGS. 5 and 6, the tracker 300, 400 may be provided at an opposed side of the grip 40, i.e. on the right side of the grip 40 with respect to FIGS. 5 and 6.

Figure 7:
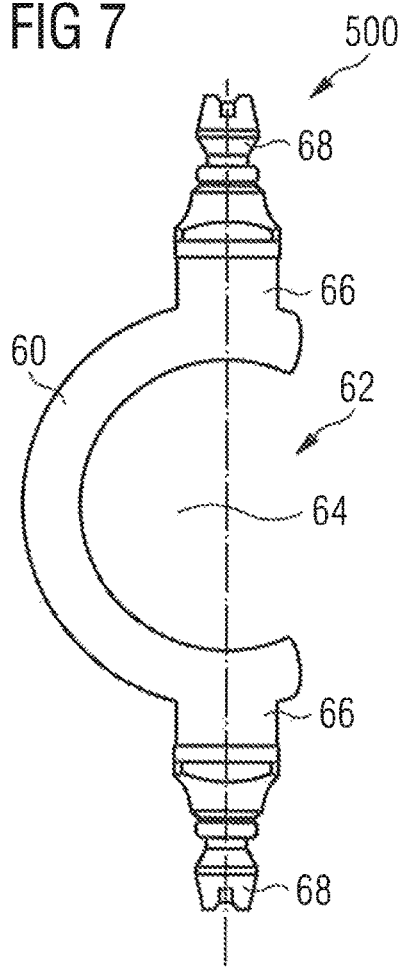
FIG. 7 shows, in a cross-sectional view, a third embodiment of a tracker.

FIG. 7 shows a planar view of another modified version 500 of the tracker 300 shown in FIG. 5. According to this modified version 500, the attachment element 60 is also configured as a sleeve, but the sleeve is open on a lateral side 62 thereof. The sleeve has an opening 64 extending along a longitudinal axis 20 of the attachment element 60 (cf. FIG. 8). The cross-section of the opening 64 is adapted to the cross-section of the surgical tool intended to be used with the tracker 500, and the dimensions of the opening 64 are such that the surgical tool can be received therein.

The attachment element 60 with a lateral side open forms a clip mechanism. In particular, the surgical tool such as a biopsy needle is not inserted into the opening 64 of the attachment element 60 so as to slide along the longitudinal axis 20 of the attachment element 60, but the tracker 500, more specifically the attachment element 60 of the tracker 500, is clipped on the surgical tool such as the biopsy needle by receiving the surgical tool via the open lateral side 62. In particular, the attachment element 60 is clipped on the surgical tool by moving it in a direction perpendicular to the longitudinal axis 20 so as to receive the surgical tool via the open lateral side. For being clippable on the surgical tool, the attachment element 60 should at least partially be made of an elastic material, for example of a plastics material such as PEEK, for example, or PPSO2, for example.

Figure 8:
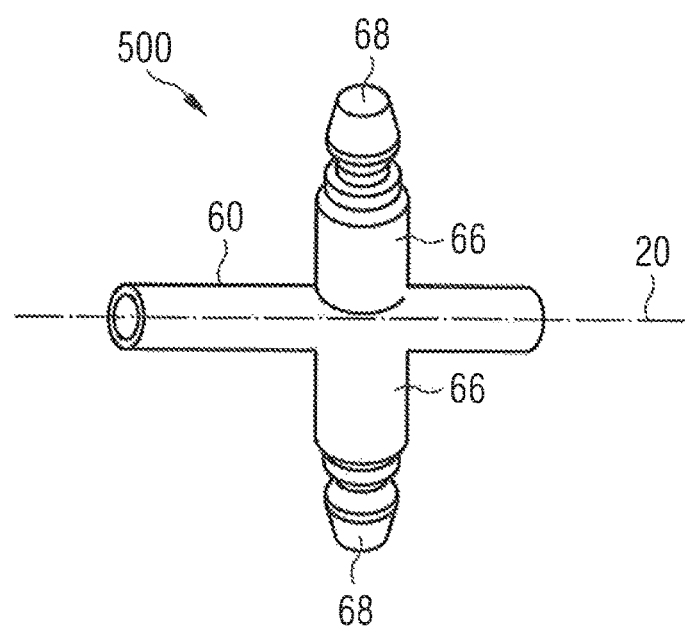
FIG. 8 shows, in a top view, the tracker of FIG. 7.

The attachment element 60 of the tracker 500 has projections 66 that extend away from the sleeve in a lateral direction (indicated by the dashed line in FIG. 7) perpendicular to the direction of the longitudinal axis 20. The tracker 500 further comprises mounting posts 68 that are connected to the projections 66 of the attachment element 60 and are configured for receiving markers (not shown here). In the embodiment of FIGS. 7 and 8, two projections 66 and two mounting posts 68 for two markers are provided. The mounting posts 68 are designed so as to be symmetrical to the longitudinal axis 20 defined by the opening extending in a longitudinal direction of the attachment element 60. Furthermore, as can be seen in the cross-sectional view of FIG. 6, the mounting posts 68 are arranged so as to be centered with respect to a middle (center) of the opening 64.

The markers can be connected to the mounting posts 68 by any known attachment mechanism. Such attachment mechanism may include threading, snap connections, and quick connections, for example. The mounting posts 68 and the attachment element can be made of the same material. They can for example both be made of PEEK. The markers may have a spherical shape as illustrated in FIGS. 1 to 5, or any other shape. Instead of being connected to the attachment element 60, the mounting posts 68 and the attachment element 60 can be configured as a one-piece part, for example as an injection-molded part.

Also in the variant of FIGS. 7 and 8, the attachment element 60 can have the function of a stopper element limiting the insertion depth of the surgical tool, in particular the insertion depth within a guiding tube or within bores of a guidance of a precision arm.

In all embodiments, the markers 12, 57 may be releasably mounted to the attachment element 14 and/or mounting posts 48, 68 (if provided) and thus can be disposed of separately from attachment element 14 and/or mounting posts 48, 68 and/or can be sterilizable separately from the attachment element 14 and/or mounting posts 48, 68. Alternatively, the markers 12 are non-releasably mounted to the attachment element 14 and/or mounting posts 48, 68.

Figure 9:
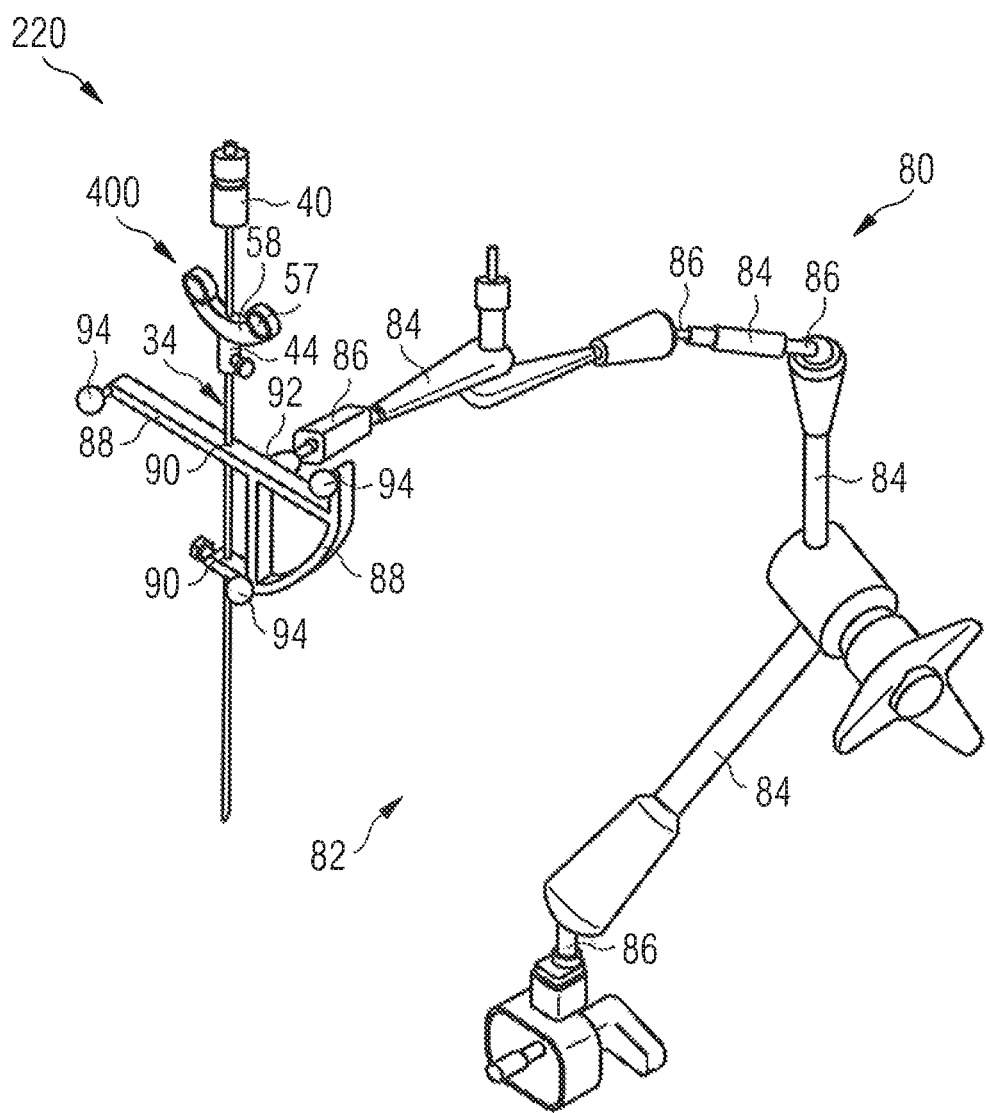
FIG. 9 shows an embodiment of a surgical guide system.

FIG. 9 shows an embodiment of a surgical guide system 80. The surgical guide system 80 includes the surgical tool system 220 of FIG. 6 with the tracker 400, but it may also include any other surgical tool system disclosed herein. The surgical guide system 80 further comprises a precision arm 82 which is three-dimensionally movable and fixable relative to a patient. For that purpose, the precision arm 82 comprises several arms 84 that are serially connected by joints 86 with each other. The precision arm 82 also comprises a guidance 88 which is coupled by a joint 86 to an adjacent arm 84. The guidance 88 comprises two bores 90 that define an insertion direction of the surgical tool system 220. The two bores 90 form the actual guiding structure. In other embodiments, a guidance tube may be used instead of the bores 90.

As can be seen in FIG. 9, a proximal stop surface 45 (cf. FIG. 6) of the stopper element 44, i.e., the surface 45 of the stopper element 44 facing the guidance 88 and being proximal to the tip 38 of the surgical tool 34, cooperates with an abutment surface 92 of the guidance 88 so as to limit the movement of the surgical tool 34 within the bores 90 in the insertion direction. Or, in other words, the placement of the stopper element 44 relative to the tip 38 of the surgical tool 34 determines an insertion depth of the surgical tool 34, i.e., how far the surgical tool 34 can be inserted into the bores 90 of the precision arm 82 (and, thus, into the patient) before it is stopped.

As can be seen in FIG. 9, the position and/or orientation of the precision arm 82 can be tracked by means of one or more markers 94 of the precision arm 82. In particular, in the embodiment of FIG. 9, the guidance 88 is equipped with one or more markers 94, more specifically, with three markers 94. By means of these markers 94, the three-dimensional position of the precision arm 82 and/or orientation of the precision arm 82 with respect to the patient's body (which is also tracked) may be determined, and the precision arm 82 may be positioned and/or oriented such that a target surgery area within the patient's body (e.g., the patient's skull) can be treated by means of a surgical tool 34 of the surgical guide system 80.

Or, in other words, the three-dimensional orientation and/or position of the precision arm 82 with respect to the patient's body may be achieved by tracking the precision arm 82 with the markers 94 thereby defining a trajectory of the surgical tool 34. The position of the stopper element 44 then defines (in one dimension) how far the surgical tool 34 may be moved along the trajectory.

Figure 10:
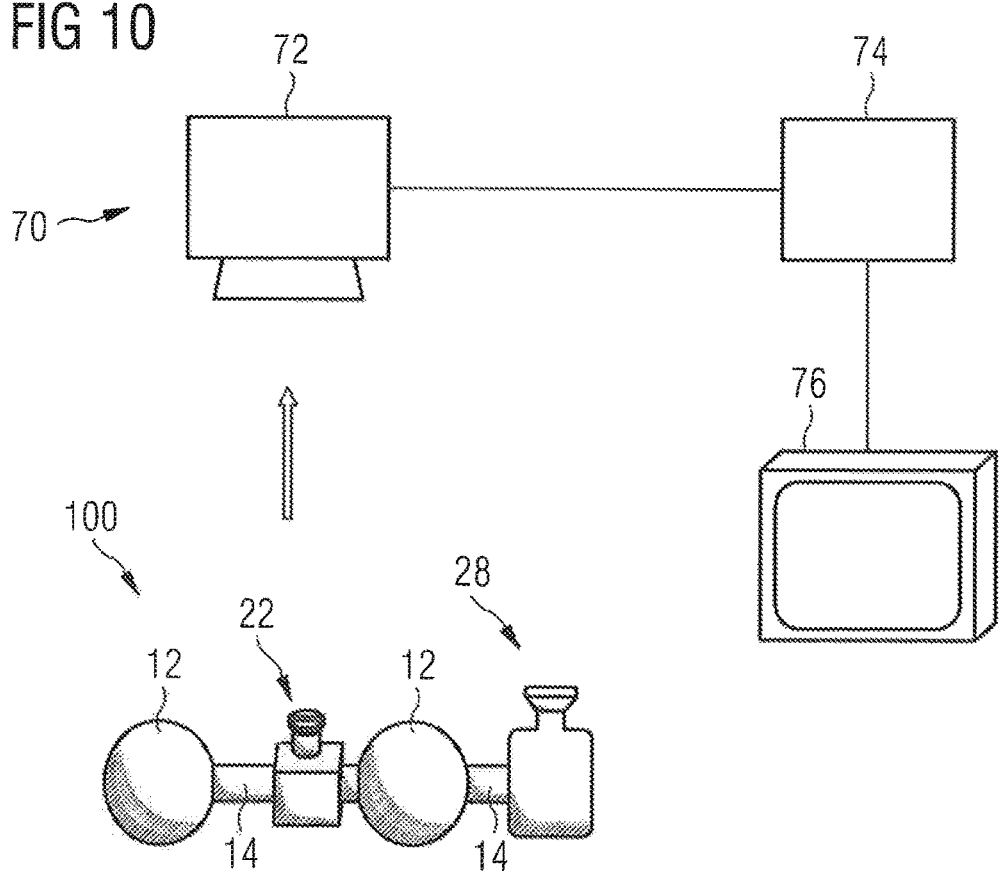
FIG. 10 shows a surgical navigation system comprising the tracker of FIG. 2

FIG. 10 shows a surgical navigation system 70 which comprises a tracker and an optical sensor 72. In FIG. 10, the surgical navigation system 70 is shown with the tracker 100 of FIG. 2. However, the surgical navigation system 70 can be used in connection with any of the tracker embodiments described herein.

The optical sensor 72 comprises a camera, such as a stereo camera. The optical sensor 72 is configured to detect a light spectrum that is reflected (in the case of passive markers) or emitted (in the case of active markers) by the plurality of markers. The optical sensor may be for example configured to detect light in the IR spectrum. In such a case, the surgical navigation system 70 is less affected by ambient light. The optical sensor is configured to generate sensor data indicative of the detected light.

The surgical navigation system 70 comprises a tracker 100 that is to be associated with a surgical tool. Alternatively, the surgical navigation system 70 may comprise a surgical tool system 200, 210, 220 as described above.

The surgical navigation system 70 further comprises a navigation controller 74 that is configured to receive the sensor data and to register or track the tracker 100 based on the received sensor data. The navigation controller 74 may be part of the optical sensor 72 or a separate device. Alternatively, the navigation controller 74 may be a separate device that is not part of the surgical navigation system 70, such as a computer that manages patient data, but that can additionally be used to compute the sensor data of the optical sensor 72.

The surgical navigation system 70 may further comprise or be connected to an output device 76. The output device 76 comprises at least one of a display, a speaker, a beamer, and a haptic feedback device. The output device 76 is configured to output information and/or instructions that result from tracking the tracker 100. The output information may comprise at least one of a visual display of the tracked tracker 100 or the associated surgical tool, a visual display of the tracker 100 or the associated surgical tool relative to registered patient data, and an acoustic signal indicative of a position of the tracker 100 (e.g., relative to a virtual boundary with respect to a patient). The instructions may comprise at least one of a visual representation of a target shape, target position and target orientation of the tracker 100, and a voice output guiding the surgeon.

Figure 11:
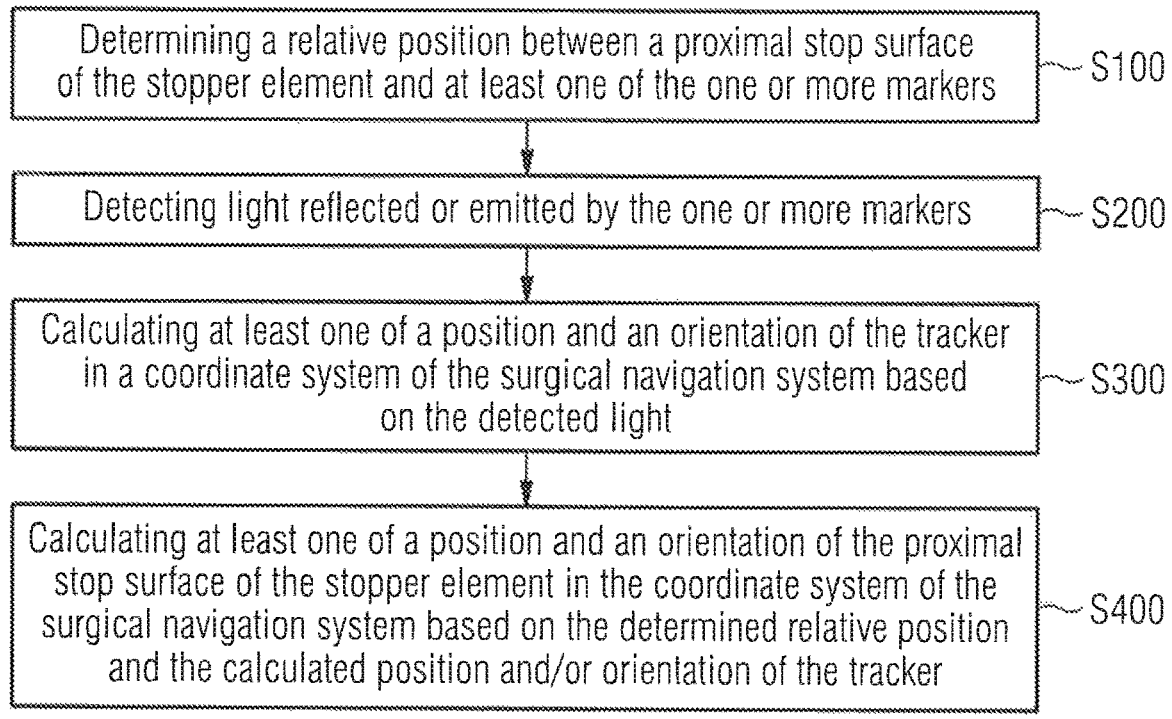
FIG. 11 shows a flow diagram of a method of operating a surgical navigation system.

FIG. 11 shows a flow diagram of an embodiment of a method of operating surgical navigation system. The surgical navigation system may be the surgical navigation system 70 of FIG. 10 with any of the trackers 100, 110, 300, 400, 500 disclosed herein that comprise an integrated stopper element. The surgical navigation system may also comprise the precision arm 82 of FIG. 9.

In step S100, a relative position between a proximal stop surface of the stopper element and at least one of the one or more markers of the tracker 100, 110, 300, 400, 500 is determined. In step S200, light reflected or emitted by the one or more markers is detected by the optical sensor. In step S300, at least one of a position and an orientation of the tracker in a coordinate system of the surgical navigation system based on the detected light is calculated. Then, in step S400, at least one of a position and an orientation of the proximal stop surface of the stopper element in the coordinate system of the surgical navigation system based on the determined relative position and the calculated position and/or orientation of the tracker is calculated.

The relative position may be defined by a distance between the proximal stop surface and the at least one marker, and how the proximal stop surface is oriented with respect to the at least one marker. Since the stopper element is part of the tracker 100, 110, 300, 400, 500, the relative position between the stopper surface and the markers may be a known or predefined variable or may be easily determined in step S100 by common means such as a ruler.

Calculating the position and/or orientation of the tracker in a coordinate system of the surgical navigation system in step S300 may include calculating the position and/or orientation of the tracker relative to the optical sensor. The calculation may be performed in one dimension (further dimensions may be processed on the basis of the markers 94 in FIG. 9). Step S400 may then include calculating the position and/or orientation of the proximal stop surface of the stopper element relative to the optical sensor.

Usually, also the patient's body is tracked by means of the optical sensor, so that the position and/or orientation of the patient's body relative to the optical sensor may be calculated. Consequently, the position and/or orientation of the proximal stop surface of the stopper element relative to the patient's body may be determined in three dimensions based on the data calculated in step S400 and the position and/or orientation of the patient's body relative to the optical sensor.

In a further method step, that is not illustrated in FIG. 11, the position and/or orientation of the proximal stop surface of the stopper element relative to a target surgery area within the patient's body may be determined. Then, in a subsequent method step, it may checked whether the position and/or orientation of the proximal stop surface of the stopper element relative to a target surgery area within the patient's body corresponds to a pre-planned target relative position and/or target relative orientation of the proximal stop surface of the stopper element relative to the target surgery area. In particular, the target relative position and/or target relative orientation of the proximal stop surface relative to the target surgery area is the position and/or orientation of the proximal stop surface with respect to the target surgery area when the tip of the surgical tool has reached the target surgery area when inserting the surgical tool into the patient's body.

In an embodiment of the method presented herein, the position of the stopper element is validated before the above described method step S100. Specifically, the tracker is coupled with the surgical tool, and the tracker may be fixed to the surgical tool so that a relative position and/or relative orientation between the proximal stop surface of the stopper element and a tip of the surgical tool corresponds to a pre-planned target value for the relative position/and or relative orientation. The target position and/or target orientation of the proximal stop surface relative to the target surgery area is the position and/or orientation of the proximal stop surface with respect to the target surgery area when the tip of the surgical tool has reached the target surgery area when inserting the surgical tool into the patient's body. In the surgical guide system of FIG. 9, the target position and/or target orientation of the proximal stop surface relative to the target surgery area is defined by the relative position and/or relative orientation between the abutment surface of the guidance and the target surgery area within the patient's body.

Hence, by way of the disclosed method, the position of the stopper element may be double checked. For example, if it is decided in step that the position and/or orientation of the proximal stop surface of the stopper element relative to a target surgery area within the patient's body corresponds to the target relative position and/or target relative orientation of the proximal stop surface of the stopper element relative to the target surgery area, the stopper element should abut against the abutment surface of the guidance. Or, vice versa, if the stopper element abuts against the abutment surface of the guidance thereby limiting a further insertion of the surgical tool, the position and/or orientation of the proximal stop surface of the stopper element relative to a target surgery area within the patient's body determined should correspond to the target position and/or target orientation of the proximal stop surface of the stopper element relative to the target surgery area. If this is not the case, an error or defect might be present. For example, the surgical tool such as the biopsy needle might be accidentally bent, or the tracker might not be correctly positioned to the surgical tool. A warning may then be output to the surgeon. Based on the specific situation, the surgeon may then decide whether he or she wants to stop an insertion of the surgical tool or whether he or she wants to continue inserting.

As has become apparent from the exemplary embodiments above, the present disclosure presents an external tracker that is designed to be symmetrical with respect to a longitudinal axis of an attachment element and, when being connected to a surgical tool like a biopsy needle, optionally also with respect to the longitudinal axis of the surgical tool coinciding with the longitudinal axis of the attachment element. In addition, compared to known solutions of external trackers, the tracker according to the present disclosure has a small footprint and is light weight. Thus, also with the tracker attached, the surgical tool is well balanced and only slightly increased in weight and can thus be handled in a familiar manner by the surgeon.

Furthermore, since the present tracker is an external tracker that can be attached to the surgical tool and is not an integrated solution, the surgeon can use the surgical tool he is used to and does not have to switch to a new, unfamiliar system.

As described above with respect to FIGS. 2 to 9, the stopper which is used to define how deep a surgical tool is allowed to go may be combined with the tracker. In an exemplary biopsy workflow, a target of the biopsy, an entry point and a trajectory may be defined (i.e., pre-planned). The depth of the target is calculated and may be used to manually adjust the stopper prior to surgery so that the biopsy window in the needle is perfectly aligned with the target. Combining the stopper with the tracker allows for double checking the placement of the stopper since the position of the tip of the needle needs to be validated anyway.

The embodiments of FIGS. 5 to 8, which provide a tracker with an attachment element configured as a clip mechanism and/or mounting posts for mounting the markers, wherein the attachment element and the mounting posts may be made of the same material and may be also configured as a one-piece part, presents a solution that is easy to manufacture and thus relatively inexpensive. Furthermore, it can be re-used since it is sterilizable.

The invention claimed is:
1. A surgical system comprising:
   a surgical tool defining a tool longitudinal axis;
   a tracker comprising:
      a plurality of markers; and
      a sleeve configured to releasably be attached to a surgical tool and having a proximal longitudinal end and a distal longitudinal end, wherein the sleeve comprises a through-opening configured for slidably receiving the surgical tool such that the surgical tool extends past the proximal and distal longitudinal ends, the through-opening defining a longitudinal axis, mounting posts or wings each having a proximal end directly coupled to the sleeve and a distal end directly coupled to one of the plurality of the markers,
   wherein each of the plurality of markers are directly coupled to each of the mounting posts or wings so as to be axisymmetrically arranged with respect to the tool longitudinal axis when the surgical tool is received within the through-opening such that the mounting posts or wings extend in a direction substantially perpendicular to the longitudinal axis of the sleeve and at least two of the plurality of markers are arranged on a common plane that extends through the tool longitudinal axis,
   wherein each of the plurality of markers is laterally arranged at a distance from the longitudinal axis of the sleeve and from the tool longitudinal axis when the surgical tool is received within the through-opening.
2. The surgical system of claim 1, wherein the sleeve is at least partially made of a flexible material so as to be clippable on the surgical tool.
3. The surgical system of claim 1, wherein the tracker further comprises a fixation member for positionally fixing the one or more markers with respect to the surgical tool, and wherein the fixation member is mounted to the sleeve.
4. The surgical system of claim 1, further comprising a stopper element configured for cooperating with a guidance so as to limit an insertion depth of the surgical tool.
5. The surgical system of claim 4, wherein the stopper element is releasably mounted to the sleeve at a longitudinal end of the sleeve or the sleeve forms the stopper element, the longitudinal end of the sleeve being the proximal longitudinal end.
6. The surgical system of claim 4, wherein the stopper element forms a fixation member for positionally fixing the plurality of markers with respect to the surgical tool.
7. The surgical system of claim 1, wherein the plurality of markers are exactly two markers.
8. A surgical system comprising:
   a surgical tool defining a tool longitudinal axis; and
   a tracker comprising a plurality of markers for determining a position of the tracker, an attachment element configured to releasably attach the tracker to the surgical tool and having a proximal end and a distal end, wherein the attachment element defines a through-opening for slidably receiving the surgical tool such that a longitudinal axis of the through-opening is coaxial with the tool longitudinal axis and the surgical tool extends through the through-opening and past the proximal end of the attachment element, and wherein each of the plurality of markers is coupled to the attachment element and defines an opening through which the surgical tool is configured to be directed for the plurality of markers to be symmetrically arranged with respect to the tool longitudinal axis with the surgical tool extending through the through-opening of the attachment element, wherein the surgical tool is configured to be releasably coupled to the tracker so that the plurality of markers is in a fixed positional relationship to the attachment element.

9. The surgical system of claim 8, wherein the tool longitudinal axis coincides with the longitudinal axis of the attachment element.

10. The surgical system of claim 8, wherein the tracker comprises a stopper element, the surgical system further comprising a precision arm having a guidance for receiving the surgical tool such that the surgical tool is linearly movable within the guidance, wherein the precision arm is configured to be moved three-dimensionally, and wherein the guidance comprises an abutment surface which cooperates with a proximal stop surface of the stopper element so as to limit a linear movement of the surgical tool within the guidance in one direction.

11. The surgical system of claim 8, further comprising an optical sensor capable of detecting light reflected or emitted by plurality of markers and of generating a sensor signal indicative of the detected light.

12. The surgical system of claim 11, further comprising a navigation controller capable of receiving the sensor signal and at least one of registering and tracking the tracker based on the received sensor signal.

13. A surgical system comprising:
   a surgical tool defining a tool longitudinal axis and having a handle grippable by a surgeon for using the surgical tool;
   a tracker comprising:
      one or more markers;
      a sleeve configured to releasably be attached to the surgical tool and having a proximal longitudinal end and a distal longitudinal end;
      a fixation member provided at the sleeve for positionally fixing the one or more markers to the surgical tool; and
      a stopper element mounted to proximal longitudinal end of the sleeve such as to form the proximal longitudinal end of the sleeve,
   wherein the sleeve and the stopper element together define a through-opening for slidably receiving the surgical tool such that a longitudinal axis of the through-opening is coaxial with the tool longitudinal axis and the surgical tool extends through the through-opening such that the handle protrudes from the distal longitudinal end of the sleeve and a tip of the surgical tool protrudes from the proximal longitudinal end of the sleeve,
   wherein the stopper element has a proximal abutment surface having greater cross-sectional dimensions than the sleeve has at the proximal longitudinal end such that the proximal abutment surface of the stopper element is configured to abut against an abutment surface of a guidance so as to limit an insertion depth of the surgical tool when the surgical tool is inserted into the guidance and with the surgical tool extending through the through-opening of the sleeve and the stopper element,
   wherein the one or more markers are coupled to the sleeve so as to be symmetrically arranged with respect to the tool longitudinal axis with the surgical tool extending through the through-opening of the sleeve and the stopper element,
   wherein the stopper element is configured to be arranged in a predefined, fixed position relative to the one or more markers, the predefined, fixed position being determined by a target value for a relative position between the one or more markers and a target surgery area.

14. The surgical system of claim 13, wherein the stopper element forms the fixation member.

* * * * *